United States Patent
Daerr et al.

(10) Patent No.: US 10,507,004 B2
(45) Date of Patent: Dec. 17, 2019

(54) PHANTOM DEVICE, DARK FIELD IMAGING SYSTEM AND METHOD FOR ACQUIRING A DARK FIELD IMAGE

(71) Applicant: KONINKLIJKE PHILIPS N.V., Eindhoven (NL)

(72) Inventors: Heiner Daerr, Hamburg (DE); Thomas Koehler, Norderstedt (DE); Hanns-Ingo Maack, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/321,504

(22) PCT Filed: Dec. 18, 2017

(86) PCT No.: PCT/EP2017/083195
§ 371 (c)(1),
(2) Date: Jan. 29, 2019

(87) PCT Pub. No.: WO2018/114734
PCT Pub. Date: Jun. 28, 2018

(65) Prior Publication Data
US 2019/0298294 A1 Oct. 3, 2019

(30) Foreign Application Priority Data
Dec. 22, 2016 (EP) .................................. 16206303

(51) Int. Cl.
*A61B 6/00* (2006.01)
*G01N 23/041* (2018.01)

(52) U.S. Cl.
CPC .............. *A61B 6/583* (2013.01); *A61B 6/484* (2013.01); *A61B 6/5205* (2013.01);
(Continued)

(58) Field of Classification Search
CPC .......... G01N 2223/3035; G01N 23/041; A61B 6/583; A61B 6/485; G21K 2207/005
See application file for complete search history.

(56) References Cited

U.S. PATENT DOCUMENTS 5,335,260 A * 8/1994 Arnold .................. A61B 6/505
378/18
2010/0278409 A1* 11/2010 Wiemker .............. A61B 6/583
382/131
(Continued)

FOREIGN PATENT DOCUMENTS

WO WO2015044238 A1 4/2015
WO WO2015180977 A1 12/2015
WO WO2017211955 A1 12/2017

OTHER PUBLICATIONS

G0cha Khelashvili et al, "A Physical Model of Multiple-Image Radiography", Physics in Medicine and Biology, Institute of Physics Publishing, Bristol GB, vol. 51, No. 2, Jan. 21, 2006 (Jan. 21, 2006).
(Continued)

Primary Examiner — Dani Fox
(74) Attorney, Agent, or Firm — Larry Liberchuk

(57) ABSTRACT

The present invention relates to phantom device for a dark field imaging system. Although dark field imaging is known to be sensitive to changes in the micro-structure of the tissue of a human subject that may be caused during a disease progression, there may be a need to quantify information provided by an image of the human subject. A detector signal component representing the dark image may be altered by changes of the X-ray spectrum which passes tissue of the human subject comprising micro-structures. This may be caused due to an attenuation of the X-ray radiation previously provided by an X-ray source, wherein
(Continued)

the attenuation may be caused by tissue of the human subject, which covers said micro-structure comprising tissue. In order to provide information in clinical practice regarding the influence of attenuation to the X-ray radiation before it passes the micro-structure issue of the human subject, the phantom device for dark field imaging is proposed. The phantom device comprises a main body, wherein the main body comprises a plurality of reference parts. Each of the reference parts comprises an attenuation part and a de-coherence part. The attenuation part and the de-coherence part of the same reference part are stacked on top of each other. As a result, the different reference parts may imitate different portions of the human subject extending along a propagation direction of an X-ray radiation, which is propagated from an X-ray source of the dark field imaging system towards the corresponding X-ray detector. Thus, if the phantom device is scanned simultaneously or subsequently with the human subject, a dark field image may be acquired, which represents the human subject as well as the phantom device. From the image parts of the dark field image caused by the phantom device, a clinician may assess and classify the corresponding parts of the image, which relates to the human subject, for instance to the portions of the lung. The present invention further relates to an imaging system configured to scan a human subject together with the phantom device as well as a corresponding method.

14 Claims, 6 Drawing Sheets

(52) U.S. Cl.
CPC ... *G01N 23/041* (2018.02); *G01N 2223/3035* (2013.01); *G21K 2207/005* (2013.01)

(56) References Cited

U.S. PATENT DOCUMENTS

2011/0243305 A1* 10/2011 Tada ............... A61B 6/4291
378/87
2015/0182185 A1* 7/2015 Klinder ............ A61B 6/032
600/426

OTHER PUBLICATIONS

Pfeiffer F et al., "Phase Retrieval and Differential Phase-Contrast Imaging with Low-Brilliance X-Ray Sources", Nature Physics, Nature Publishing Group, London, GB, vol. 2 , Mar. 26, 2006 (Mar. 26, 2006), pp. 258-261, XP002518081.

Donath T. et al., "Inverse Geometry of Grating-Based X-Ray Phase-Contrast Imaging", Journal of Applied Physics 106, 054703, Oct. 2009.

Yashiro W. et al., "On the Origin of Visibility Contrast in X-Ray Talbot Interferometry" Optics Express, vol. 18, No. 16, pp. 16890-16901, Aug. 2010.

* cited by examiner

PHANTOM DEVICE, DARK FIELD IMAGING SYSTEM AND METHOD FOR ACQUIRING A DARK FIELD IMAGE

FIELD OF THE INVENTION

The present invention relates to a phantom device for a dark field imaging system, a dark field imaging system, a method for acquiring an image, a computer program element and a computer-readable medium.

BACKGROUND OF THE INVENTION

In conventional X-ray imaging, contrast in an image is usually achieved by an attenuation of X-ray radiation in an object to be imaged. Over the past decade, several techniques have been developed to exploit the contrast given by a phase-shift of X-ray radiation transmitted through the object. X-ray photons of the X-ray radiation may be absorbed, coherently refracted and/or scattered. Whether the X-ray photons are absorbed, coherently refracted or scattered, the respective interaction may be used to form a respective image or an image component of a multi-component image. To acquire this information, a dark field imaging system may be used. Such a system comprises a source for generating X-ray radiation, a detector for detecting X-ray radiation and an interferometer arranged between the source and the detector for creating interference pattern. The interferometer may be formed by a Talbot grating interferometer. Such an interferometer may comprise an absorbing source grating, a phase grating and an analyzer grating. The gratings are arranged one after the other in an X-ray beam path between the source and the detector. Further, an object receiving space is arranged between the source and the detector, in particular between two of the gratings of the interferometer. The phase grating may be formed to introduce a phase-shift of an incoming X-ray beam (formed by X-ray radiation of the source) which creates an interference pattern behind the phase grating.

Furthermore, it is to be considered that an X-ray beam imposed on a subject, in particular a human subject, positioned at the object receiving space may cause an attenuation, a scattering and/or a refraction of the X-ray beam. In principle, the dark field imaging system may be configured to acquire image data via the detector representing an attenuation, a scattering and/or refraction caused by the subject. The refraction caused by the subject may be determined based on the displacement of the interference fringes. However, as the interference fringes may not be spatially resolved with a conventional X-ray detector, the acquiring of measurement data may be performed by using a phase-stepping technique. In this context, the X-ray radiation intensity oscillation behind the analyzer grating during a lateral stepping scan of one of the gratings is recorded and the fringe displacement is determined in terms of the phase-shift of the oscillation curve of each of the plurality of detector pixels of the X-ray detector. The measured phase-shift of the intensity oscillation in each detector pixel may relate to the local refraction angle, a distance between the phase grating and the analyzer grating, and a period of the analyzer grating. In this context, reference is made to the document "Inverse geometry of grating-based X-ray phase-contrast imaging", Journal of Applied Physics 106, 054703 (2009).

Based on the detector signal provided by the X-ray detector, three images may be determined representing an object to be imaged. The object is preferably a human subject. The first image may be referred to as the conventional image or the attenuation image. The conventional image may be determined based on a component of the detector signal representing the attenuation imposed on the X-ray radiation transmitted through the object. The attenuation imposed on an X-ray beam may also be referred to as an attenuation disturbance caused to an X-ray beam. The second image may be referred to as the dark field image. The X-ray detector signal may comprise a component representing a scattering imposed on the X-ray radiation transmitted through the object. As the scattering may cause de-coherence to the respective X-ray beam, the scattering may also be referred to as a de-coherence disturbance caused to an X-ray beam. The dark field image may be determined based on a component of the detector signal representing the de-coherence imposed on the X-ray radiation transmitted through the object. The third image may be referred to as the differential phase contrast image. The X-ray detector signal may comprise a component representing a refraction imposed on the X-ray radiation transmitted through the object. The differential phase contrast image may be determined based on a component of the detector signal representing the refraction imposed on the X-ray radiation transmitted through the object. As a result, three images may be determined, namely a differential phase-contrast image based on the refraction imposed on the X-ray beam, a dark field image based on the scattering imposed on the X-ray beam and a conventional image based on the attenuation imposed on the X-ray beam.

Document WO 2015/180977 A1 discloses a phantom body for the use in a phase-contrast imaging system for calibrating the phase-contrast imaging system. The phantom body comprises three mutually distinct and separately arranged parts. A first part of the phantom device is configured to cause a phase-shift disturbance. A second part of the phantom device is configured to cause an absorption disturbance. A third part of the phantom body is configured to cause a de-coherence disturbance. Each of said disturbances relates to an X-ray beam, when said X-ray beam passes through the phantom body. As a result, each of the parts of the phantom body exclusively responds to exactly one of the respective three disturbance effects. Thus, the phantom body allows to calibrate the phase-contrast imaging system, in particular with respect to three different images to be acquired, namely the conventional image, the differential phase-contrast image and the dark field image.

SUMMARY OF THE INVENTION

It has been found that a dark field image often provides relevant information, especially for lung imaging. In order to identify changes of a region of interest of a human subject, several dark field images may be acquired at different time instances. For example, a first dark field image may be acquired at a first lung disease stage, wherein after a while, a follow-up dark field image may be acquired in order to examine the possible changes of the disease. In practice, it is often not certain, that the same calibrated dark field imaging device is used with the same settings in order to acquire the respective dark field images. As a result, even if the region of interest of the subject (in particular its lung) may not have changed between the acquisition instances, differences in the respective dark field images may occur. This results for instance from different settings of the dark field imaging system at the different acquisition instances. For example, different X-ray tube acceleration voltages may have been used and/or other filtration settings may have been applied. Therefore, even if each dark field imaging system is calibrated, there may be a need for a solution, which allows to reliably and quantitatively compare dark field images acquired at different scans and/or acquisition instances, even if different settings for a dark field imaging system were used.

The object of the present invention is solved by the subject-matter of each of the independent claims. Further embodiments are incorporated in the dependent claims. It should be noted that the following described aspects of the invention apply also for the phantom device, the system, the method, the computer program element and the computer-readable medium.

According to a first aspect of the invention, a phantom device for a dark field imaging system is provided. The phantom device comprises a main body. The phantom device further comprises reference parts formed of an attenuation part and a de-coherence part being stacked on the attenuation part, such that the attenuation part of the respective reference part and the de-coherence part of the same respective reference part are arranged consecutively along a predefined direction of the main body. Each de-coherence part is configured to cause de-coherence disturbance to an X-ray beam, if said X-ray beam passes the respective de-coherence part along the predefined direction. Each attenuation part is configured to cause attenuation disturbance to an X-ray beam, if said X-ray beam passes the respective attenuation part along the predefined direction. The main body comprises a first group of at least two reference parts. Each of the de-coherence parts of the first group are configured to cause the same first degree of de-coherence disturbance. The attenuation parts of the first group are configured to cause mutually different degrees of attenuation disturbance.

In an example, the dark field image system may be configured to determine a dark field image based on a detector signal representing detected X-ray radiation, which previously passed the main body. In a further example, the dark field imaging system may also be referred to as a phase-contrast X-ray imaging system or an X-ray imaging system.

In an example, the main body may be an at least basically solid body or an at least basically solid device body. The main body comprises at least the first group of the at least two reference parts. The reference parts may be integrated in the main body. For this purpose, the reference parts may be arranged in a cured resin of the main body. The cured resin may form the outer surfaces of the main body. In an example, the cured resin of the main body may be configured to cause an attenuation disturbance and/or de-coherence disturbance, wherein each of said disturbances is at least by a factor 10 smaller than a de-coherence disturbance and attenuation disturbance, respectively, caused by each of said reference parts. As a result, the attenuation disturbance and/or the de-coherence disturbance caused by the cured resin of the main body may be neglected for a further assessment.

In an example, the de-coherence part and the attenuation part of the same reference part are arranged, such that said attenuation part is directly stacked on and/or directly attached to the respective de-coherence part. As a result, the de-coherence part and the attenuation part of the same reference part may be attached gap-free to each other.

In an example, each attenuation part is configured to cause attenuation disturbance to an X-ray beam, wherein respective attenuation disturbance comprises absorption disturbance imposed on said X-ray beam. In an example, an attenuation disturbance may be formed by absorption disturbance. The absorption disturbance may also be referred to as absorption. In a further example, each attenuation part may be formed by a respective absorption part and/or at least comprises a respective absorption part. In the latter case, the absorption part may also be referred to as an absorption sub-part. In an example, each attenuation part, in particular formed as a respective absorption part, is configured to absorb X-ray radiation. In an even further example, each attenuation part may be configured to cause attenuation disturbance to an X-ray beam, wherein the respective attenuation disturbance may comprise Compton scattering disturbance imposed on said X-ray beam. In an example, each of said attenuation disturbance may be formed by the respective Compton scattering disturbance. In a further example, each attenuation part may be formed by a Compton scattering disturbance part or comprises a Compton scatter disturbance sub-part. In a further example, each attenuation part is configured to cause attenuation disturbance to an X-ray beam, wherein a respective attenuation disturbance comprises absorption disturbance and Compton scatter disturbance. In an even further example, the respective attenuation disturbance may be formed by absorption disturbance and Compton scatter disturbance.

In an example, each de-coherence part is configured to cause de-coherence disturbance to an X-ray beam, wherein the respective de-coherence disturbance may relate to scattering disturbance imposed on said X-ray beam, if said X-ray beam passes the respective de-coherence part. Thus, the de-coherence disturbance may also be referred to as scattering disturbance. In an example, the degree of de-coherence disturbance relates to the reduction of a degree of coherence between a first X-ray beam and a second X-ray beam, if the first X-ray beam represents an X-ray beam passing in a de-coherence part and if the second X-ray beam represents the respective X-ray beam passing out said de-coherence part.

In an example, the reference parts of the same group, in particular of the first group, are arranged in parallel to each other. As a result, the attenuation part and the de-coherence part of each common respective reference part may be arranged consecutively along the predefined direction of the main body. Thus, X-ray radiation propagated along the predefined direction of the main body passes each of the reference parts along the predefined direction of the main body. The predefined direction of the main body may therefore also be referred to as a propagation direction of the main body or as a propagation direction. The propagation direction may correspond to the propagation direction of X-ray radiation provided by a source of the dark field imaging system. As a result, this may be ensured that X-ray radiation provided by a source of the dark field imaging system passes each reference part along the predefined direction of the main body and therefore passes the attenuation part and the de-coherence part of each respective reference part consecutively along the predefined direction of the main body.

In an example, the reference parts of each group, in particular of the first group, are mutually spaced apart from each other. As a result, X-ray radiation passing through each of the reference parts may be distinguished from each other based on the spatial relation of the respective reference parts.

In an example, the de-coherence parts of the first group relate to the de-coherence parts of the reference parts of the first group. In an example, the attenuation parts of the first group relate to the attenuation parts of the reference parts of the first group.

A preferred advantage of the phantom device according to the first aspect of the present invention should be outlined exemplarily in the following. For example, if a human subject of interest is placed at an object receiving space of the dark field imaging system, the X-ray radiation provided by a source of the dark field imaging system may relate to a corresponding wavelength spectrum. If said X-ray radiation is propagated towards the human subject, the X-ray radiation may initially pass material of a first area of the human subject, wherein said material may cause an attenuation to the X-ray radiation. The attenuation may depend on the density of said material, on the length in a propagation direction of said material and/or on other properties of said material at said area of the subject. As a result, X-ray radiation passing out of said first area and thereafter passing in a further, second area of the human subject, wherein the material at the second area of the human subject may cause for example de-coherence disturbance. The de-coherence disturbance may depend on several conditions, in particular on the spectrum of the X-ray radiation passing through the material of the second area. As an effect, the de-coherence disturbance imposed on the X-ray radiation passing through the second area may be different for different wavelength spectra.

The phantom device according to the first aspect of the present invention allows to cause similar disturbances to an X-ray beam with respect to disturbances caused by a human subject, in particular with regard to disturbances caused from different sections of a lung region of the human subject. A section of the lung region does not refer to a physical section, segment or slice of a lung region, but may rather refer to a cross-sectional region of the lung region.

The phantom device may be scanned together with a region of interest of a human subject resulting in a dark field image representing with a first image section the region of interest of the human subject and with a second image section the phantom device.

Since the main body of the phantom comprises at least the first group with at least two reference parts, wherein the attenuation parts of the first group are configured to cause mutually different degrees of attenuation disturbance, the resulting effects of the de-coherence disturbance allow an enhanced evaluation of the first image section of the dark field image representing the region of interest of the human subject.

In particular, the attenuation parts of the first group are configured to cause mutually different degrees of attenuation disturbance and therefore may result in a corresponding change of a wavelength spectrum. The respective wavelength spectrums may be mutually different. As a result, the de-coherence parts of the first group may be subject to X-ray radiation, wherein each of said X-ray radiation passing the respective reference part may relate to a different wavelength spectrum. Thus, each of the de-coherence parts may be passed by X-ray radiation with mutually different wavelength spectra. As this effect is similar to the one previously described with regard to the different body regions of the human subject, a better and more reliably assessment of the image section of the dark field image representing the human subject or its region of interest may be carried out.

As an even further effect, if a region of interest of a human subject is scanned several times together with the phantom device resulting in a respective number of dark field images, the dark field images may differ for instance due to a use of different dark field imaging systems and/or due to different settings of the same dark field imaging system. However, since each dark field image represents also the phantom device by a respective section of said image, the respective section may—for each corresponding dark field image—provide a basis to identify differences due to said reasons and/or may be used as a basis for a better and/or more reliable assessment of the section of the respective dark field image representing the human subject, or its region of interest. For example, if a lung as a region of interest of the human subject did not change between two scans, but if the dark field imaging system is operated with different X-ray tube accelerate voltages, the absolute image values of the resulting two dark field images may not be the same but be different. But both dark field images may be reliably assessed and/or classified by using the section of the respective dark field image representing phantom device as a reference, in particular for the image values.

According to an exemplary embodiment of the phantom device, the main body comprises also a second group of at least two reference parts. Each of the de-coherence parts of the second group is configured to cause the same second degree of de-coherence disturbance. The attenuation parts of the second group are configured to cause mutually different degrees of attenuation disturbance. The de-coherence parts of the first and second group are configured, such that the first degree of de-coherence disturbance is different from the second degree of de-coherence disturbance.

With respect to each reference part of the second group, it may be noted, that—as previously explained—each reference part is formed from an attenuation part and a de-coherence part being stacked on the respective attenuation part, such that the respective attenuation part and the respective de-coherence part of the respective reference part are arranged consecutively on the predefined direction of the main body. Furthermore, it may be noted, that each de-coherence part is configured to cause (the respective) de-coherence disturbance to an X-ray beam, if said X-ray beam passes the respective de-coherence part along the predefined direction. It may further be noted, that each attenuation part is configured to cause (the respective) attenuation disturbance to an X-ray beam, if said X-ray beam passes the respective attenuation part along the predefined direction.

In an example, the de-coherence parts of the second group relate to the de-coherence parts of the reference parts of the second group. In a further example, the attenuation parts of the second group relate to the attenuation parts of the reference parts of the second group.

As an effect, the main body comprises a first group and a second group, wherein each of said groups comprises at least two reference parts. Furthermore, the de-coherence parts of the first group and the de-coherence parts of the second group are configured that the first degree of de-coherence disturbance, which may be caused by each of the de-coherence parts of the first group, is different from the second degree of de-coherence disturbance, which may be caused by each of the de-coherence parts of the second group. Preferably, the first degree of de-coherence disturbance is higher than the second degree of de-coherence disturbance, or vice versa.

As an effect, the disturbances, which may be caused by the reference parts of the first group, may be different from the disturbances, which may be caused from the reference parts of the second group. As a result, a dark field image may comprise a section representing the different disturbances. As an effect, the respective different disturbances may be used to assess and/or classify image values of another section of the dark field image representing at least a region of interest of a human subject. In particular, a more precise assessment and/or classification of the image values may be carried out.

According to a further exemplary embodiment of the phantom device, the main body of the phantom device comprises a third group of at least two different reference parts, wherein each of the de-coherence parts of the third group are configured to cause the same third degree of de-coherence disturbance, wherein the attenuation parts of the third group are configured to cause mutually different degrees of attenuation disturbance, and wherein the de-coherence parts of the first, second and third group are configured, such that the first degree of de-coherence disturbance, the second degree of de-coherence disturbance and the third degree of de-coherence disturbance are mutually different.

In an example, the main body of the phantom device comprises even at least one further group of at least two reference parts. The at least further group may be configured and/or formed in an analogous manner as the second group or the third group. As an effect, an even more precise assessment and/or clarification of image values of a dark field image may be performed, when said image values relate to the human subject and/or a region of interest of the human subject.

According to a further exemplary embodiment of the phantom device, each group comprises at least three reference parts. As an effect, a graduation between the disturbances provided by each group may be increased.

According to a further exemplary embodiment of the phantom device, each reference part comprises a constant cross-section in a plane perpendicular to the predefined direction. In an example, the cross-section may comprise a rectangular-shape. In a further example, each reference part comprises a constant rectangular cross-section along the predefined direction. In an even further example, each reference part may comprise a cuboid-shape. As an effect, the disturbance applied to an X-ray beam passing through a reference part may not depend on a lateral position of said X-ray beam. Instead, each X-ray beam passing through the same reference part in the predefined direction may be subject to the same disturbance. Thus, an X-ray beam passing a reference part at an edge section of the reference part may be subject to a similar or equivalent disturbance as an X-ray beam passing the respective reference part centrally.

According to a further exemplary embodiment of the phantom device, each de-coherence part comprises a micro-structure configured to cause scattering, preferably small-angle X-ray scattering, to an X-ray beam, if said X-ray beam passes the respective de-coherence part in the predefined direction. In an example, the micro-structure of each de-coherence part comprises a structure size configured to cause the scattering of X-ray radiation. In an example, the micro-structure of each de-coherence part may be configured to cause a scattering angle, which is smaller than 0.1 mrad or smaller than 1.5 mrad. In a further example, the small-angle X-ray scattering may also be referred to as SAXS. In a further example, the small-angle X-ray scattering may also be referred to X-ray scattering with a scattering angle smaller than 0.1 mrad or smaller than 1.5 mrad.

As an effect, the micro-structure of a de-coherence part may be configured to cause similar disturbance, as it may be caused by lung section of a human subject. The micro-structure usually cannot be resolved by the imaging system. The spatial resolution of the detector of the imaging system is often too low to image the micro-structure. In particular, the micro-structure may cause similar disturbance as it may be imposed to a similar X-ray beam, if it passes an alveoli or a wall of an alveoli of a lung of a human subject. Depending on the healthy stage of a lung and/or of its alveoli, a lung may cause different de-coherence disturbance, if an X-ray beam passes the lung and/or said alveoli. In order to cause de-coherence disturbances in accordance with different healthy stages of a lung, the micro-structure of the de-coherence parts of the first group may cause a different de-coherence disturbance than the micro-structures of the de-coherence parts of the second group. As a result, a section of a dark field image representing the phantom device may provide a basis to assess and/or classify a section of the dark field image representing a lung of the human subject.

According to a further exemplary embodiment, the micro-structure of each de-coherence part is formed by a porous structure, in particular by a sponge-like structure.

According to a further exemplary embodiment, the micro-structure of each de-coherence part is formed by a plurality of micro-spheres integrated in a resin of the respective de-coherence part. The micro-spheres might be filled with a solid material gas with different mass density and/or electron density as the resin e.g. air. In an example, each a micro-sphere may refer to or may be formed by a spherical particle or a globular particle. In a further example, the resin preferably refers to a cured resin, in particular a cured epoxy resin. In an example, each micro-structure comprises at least 200 micro-spheres, in particular more than 1000 micro-spheres.

As an effect, the micro-spheres may cause de-coherence disturbance to an X-ray beam similar to the de-coherence caused to an equivalent X-ray beam passing a lung of a human subject. Thus, the de-coherence part of each reference part may be used to assess and/or classify image values, which may represent a respective part of a human subject, in particular a part of a lung of the human subject.

According to a further exemplary embodiment of the phantom device, the micro-spheres of the first group are each formed by and/or filled with a first material, wherein the micro-spheres of the second group are each formed by and/or filled with a second material, and wherein the first material is different from the second material. In an example, the first material has a different density than the second material. In this case, the first and second material may be of the same material type. In a further example, the type of the first material may be a different to the type of the second material. Thus, the density and/or the type of the materials may be used to advantageously adapt the de-coherence disturbance.

In an example, the micro-spheres of the first group relate to the micro-spheres of the de-coherence parts of the reference parts of the first group. In an example, the micro-spheres of the second group relate to the micro-spheres of the de-coherence parts of the reference parts of the second group. In a further example, each micro-sphere is preferably solid or may be filled with gas.

As an effect, the de-coherence parts of the reference parts of the first group may be of advantage for assessing and/or classifying a first area of the human subject, wherein the de-coherence parts of the reference parts of the second group may be of advantage to assess and/or classify a different, second area of the human subject.

According to a further exemplary embodiment of the phantom device, a size of each of the micro-spheres is between 10 μm and 300 μm. In an example, a size of a micro-sphere preferably refers to a structure size of the micro-sphere, in particular to its average outer diameter. In an example, the size of each micro-sphere is between 170 μm and 230 μm. As an effect, the sizes of the micro-spheres may be similar to the size of an alveoli of a human subject. As a result, the respective de-coherence parts may cause similar de-coherence disturbance to an X-ray beam, if the same X-ray beam passes human alveoli. As an even further effect, the de-coherence disturbance caused by a de-coherence part to an X-ray beam may provide a reliable basis in order to assess image values of a dark field image, which relate to human alveoli of the human subject.

According to a further exemplary embodiment of the phantom device, the micro-spheres of the same group are each of the same size. In an example, a same size of micro-spheres preferably relates at least basically to the same size of micro-spheres. As an effect, the micro-spheres of the de-coherence parts of the reference parts of the same group are of the same size. Since the attenuation parts of the same group are preferably configured to cause mutually different degrees of attenuation disturbance, the resulting disturbance of the reference parts of the same group may provide a basis in order to distinguish, assess and/or classify material of the human subject, wherein said material may be covered by tissue of the human subject causing mutually attenuation disturbance, if similar X-ray radiation is propagated to the human subject and the phantom device. For instance, healthy alveoli being arranged at different depths within the human subject may—due to the varying thickness of the material covering the alveoli—may be differently represented in a dark field image. Similar disturbance may be caused by the different reference parts of the same group of the body region of the phantom device. Thus, image values of the dark field image representing at least a part of a region of interest of the human subject may be assessed and/or classified with a higher reliability.

According to a further exemplary embodiment of the phantom device, the micro-spheres of the first group and the micro-spheres of the second group are of different size. In an example, a size of each of the micro-spheres of the first group may be between 170 μm and 190 μm. In an example, a size of each of the micro-spheres of the second group may be between 190 μm and 210 μm or between 210 μm and 230 μm. In an example, a size of each of the micro-sphere of the second group is between 210 μm and 230 μm and a size of each of the micro-spheres of the third group is between 190 μm and 210 μm.

According to a further exemplary embodiment of the phantom device, the micro-spheres of the first group and the micro-spheres of the second group are of same size but with a different number of micro-spheres. The same preferably holds in an analogous manner for the respective de-coherence parts. The number of micro-sphere per area may be changed by adapting, in particular increasing, the length of the respective de-coherence part along the predefined direction of the main body, which may correspond to the X-ray path of the imaging system, and/or by adapting, in particular changing, the density of the micro-spheres, in particular by the respective number of micro-spheres per volume (for example cubic centimetre).

As an effect, the micro-spheres of each group may be of advantage to cause similar de-coherence disturbance. In an example, the micro-spheres of the first group may be configured to cause a disturbance similar to healthy alveoli. In a further example, the micro-spheres of the second group may be configured to cause de-coherence disturbance similar as it may be caused by unhealthy alveoli, in particular in with respect to an early or later stage.

According to an exemplary embodiment of the phantom device, the micro-structures of each of the de-coherence parts of the same group comprise the same number of micro-spheres. As a result, the comparability and/or reproducibility of de-coherence disturbance may be enhanced. In an example, the same number of micro-spheres may refer to at least basically the same number of micro-spheres.

According to an exemplary embodiment of the phantom device, the reference parts are integrated into and/or surrounded by a casting compound of the main body. As an effect, a parallel arrangement of the reference parts may be securely provided. Furthermore, the operability of the phantom device may be enhanced.

According to an exemplary embodiment of the phantom device, the phantom device and/or its main body comprises a visible mark indicating a predefined direction of the main body. As an effect, a predefined and/or correct arrangement of the phantom device in an object receiving space of the dark field imaging system may be ensured. In particular, the visible mark allows to arrange the phantom device in the object receiving space, in order to ensure that X-ray radiation provided by the X-ray source of the dark field imaging system is propagated in a direction along the predefined direction of the main body. As an effect, each of the reference parts may be subject to a similar propagation of X-ray radiation. Furthermore, the reproducibility of a scan via the dark field imaging system using the phantom device may be increased.

According to a second aspect of the present invention, a dark field imaging system is provided. The dark field imaging system comprises a source for generating X-ray radiation, a detector for detecting X-ray radiation, a phantom device as previously explained, an object receiving space arranged between the source and the detector, a support device for supporting a human subject and/or the phantom device, an interferometer for creating interference pattern, a control unit for controlling the source and the interferometer, and a processing unit coupled to the detector for receiving a detector signal from the detector representing detected X-ray radiation. The support device is arrangeable at the receiving space, such that X-ray radiation generated by the source and transmitted through the human subject and the phantom device is/are detectable by the detector. The receiving space may also be referred to as an object receiving space. In an example, the human subject or a region of interest of the human subject may be arranged at the receiving space without the support of the support device 20. In this case, just die phantom device may be supported by the support device. In a further example, both, the human subject (or at least a region of interest thereof) and the phantom device 10 may be supported by the support device 20. The interferometer is arranged between the source and the detector. The control unit is configured to cause a scan of a region of interest of the human subject and the phantom device, such that X-ray radiation generated by the source is projected towards the region of interest of the human subject and the phantom device. The control unit is configured to control the interferometer, such that the interferometer influences X-ray radiation transmitted through the region of interest of the human subject and/or the phantom device. The processing unit is configured to determine an image, representing the region of interest of the human subject and the phantom device, based on a de-coherence component of the detector signal of the detector caused by the scan.

It is understood that, without repeating here all the explanations, examples, effects, features and/or advantages provided with reference to the phantom device, the system of the invention is intended to be configured to cause a scan by using the phantom device as described above. Thus, all the explanations, examples, effects, features and/or advantages, although provided with reference to the phantom device, are also to be intended as being provided by the system according to the present invention, in particular at least in an analogous manner. This may be achieved, if the phantom device according to the present invention is arranged simultaneously with the human subject, or at least the region of interest thereof, at the object receiving space, such that X-ray radiation provided by the X-ray source is subsequently or simultaneously propagated towards the phantom device and the human subject, in particular its region of interest thereof. As a result, the detector signal of the detector caused by a respective scan may represent both, the scanned phantom device and the scanned human subject (or its region of interest). Further, the detector signal may provide a de-coherence component, which may represent the dark field component of the image. Thus, the corresponding dark field image may be determined by the processing unit based on the de-coherence component of the detector signal.

In an example, the source may also be referred to as an X-ray radiation source or as an X-ray source.

In an example, the image, which may be determined by the processing unit, may also be referred to as a dark-field image. In an example, said image may be a tomographic image or a projection image.

In a further example, the interferometer comprises a plurality of gratings, preferably at least one source grating, at least one phase grating and at least one analyser grating. In an example, the interferometer or at least one grating of the interferometer is arranged between the object receiving space and the detector. Thus, the gratings of the interferometer may be arranged in a pathway between the source and the detector. In particular, the phase grating and/or the analyser grating may be arranged between the object receiving space and the detector. The source grating of the interferometer may be arranged between the X-ray radiation source and the object receiving space. In an example, one of the grating, in particular the analyzer grating, may be integrally formed by the detector or may be formed as a respective grating directly connected to the detector. In this context, a grating, in particular the analyser grating, assigned to the detector may be understood as a grating of the interferometer and/or as a grating arranged between the detector and the object receiving space or the source, respectively.

It is understood that, without repeating here all the explanations, examples, effects, features and/or advantages provided in the background paragraphs with reference to the interferometer and/or the gratings, the system of the invention is intended to be preferably configured to implement the interferometer and/or the gratings in an analogous manner. Thus, all respective explanations, examples, effects, features and/or advantages may also to be intended as being provided by the system according to the present invention, in particular at least in an analogous manner.

According to a third aspect of the present invention, a method for acquiring an image is provided. The method comprises at least the following steps a) and b):
a) Performing a scan of a region of interest of a human subject and a phantom device as described above, wherein step a) comprises at least the following sub-steps a.1), a.2) and a.3):
a.1) Generating X-ray radiation by a source, such that the X-ray radiation is propagated or transmitted towards the region of interest of the human subject and the phantom device resulting in transmitted X-ray radiation,
a.2) Influencing the transmitted X-ray radiation by an interferometer resulting in influenced X-ray radiation, and
a.3) Detecting the influenced X-ray radiation by a detector resulting in a detector signal; and
b) Determining an image, representing the region of interest of the human subject and the phantom, based on a de-coherence component of the detector signal.

It is understood that, without repeating here all the explanations, examples, effects, features and/or advantages provided with reference to the phantom device or the system, the method of the invention may be intended to be configured to carry out the method steps for which the system is configured to. Thus, all the above explanations, examples, effects, features and/or advantages, although provided with reference to the phantom device or the system, are also to be preferably intended as being provided by the method in an analogous manner.

According to a fourth aspect of the present invention, a computer program element is provided, which, when being executed by a processing unit, is adapted to carry out the method described above.

According to a fifth aspect of the present invention, a computer-readable medium having stored thereon a program element is provided, which, when being executed by a processing unit, is adapted to carry out the method described above.

According to an aspect of the invention, a phantom device for a dark field imaging system is provided. Although dark field imaging is known to be sensitive to changes in the micro-structure of the tissue of a human subject that may be caused during a disease progression, there may be a need to quantify information provided by an image of the human subject, if the image represents a dark field image. In particular, there may be a need to quantify a staging of a disease. The contrast of a dark field image or the detector signal comprising at least a component representing the dark field image is based on spatial changes of an X-ray beam front due to unresolved micro-structures in the tissue of the human subject. In particular, a reduction of a fringe visibility may be quantitatively related to the structure of micro-structures within said tissue. The detector signal component representing the dark field image may depend on the number and/or the size of micro-structures seen by an X-ray beam if transmitted through said structure.

Further, a detector signal component representing the dark field image may be altered by changes of the X-ray spectrum which passes tissue of the human subject comprising micro-structures. This may be caused due to an attenuation of the X-ray radiation previously provided by an X-ray source, wherein the attenuation may be caused by tissue of the human subject, which covers said micro-structure comprising tissue. As a result of the attenuation and the resulting change in X-ray spectrum, the detector signal component representing the dark field image may be influenced depending on the degree of the attenuation.

In order to provide information in clinical practice regarding the influence of attenuation to the X-ray radiation before it passes the micro-structure issue of the human subject, a phantom device for dark field imaging is proposed. The phantom device comprises a main body, wherein the main body comprises a plurality of reference parts. Each of the reference parts comprises an attenuation part and a de-coherence part. The attenuation part and the de-coherence part of the same reference part are stacked on top of each other. In particular, the attenuation part of a reference part is stacked above (or below) and on top (or below) of the respective de-coherence part. It is preferred that each of the de-coherence parts of the reference parts are configured to cause the same degree of de-coherence disturbance. The attenuation parts of the different reference parts are configured to cause mutually different degrees of attenuation disturbance. As a result, the different reference parts may imitate different portions of the human subject extending along a propagation direction of an X-ray radiation, which is propagated from an X-ray source of the dark field imaging system towards the corresponding X-ray detector. The imitation primarily relates to the disturbances in the sense of attenuation disturbance and de-coherence disturbance. For instance, a lung of a human subject may be covered with tissue of different thickness at different positions, wherein the alveoli of the lung may have at least a similar size. If the lung of the human subject is of interest for X-ray imaging, a detector signal of the dark field imaging system may represent a dark field image representing the alveoli other than in real. This may results from an uneven distribution of tissue covering the alveoli, which causes the respective different attenuation disturbance. The phantom device provides similar disturbance, since each of the de-coherence parts cause the same degree of de-coherence disturbance, wherein the attenuation parts cause mutually different attenuation disturbance. Thus, if the phantom device is scanned simultaneously or subsequently with the human subject, a dark field image may be acquired, which represents the human subject as well as the phantom device. From the image parts of the dark field image caused by the phantom device, a clinician may assess and classify the corresponding parts of the image, which relates to the human subject, for instance to the portions of the lung.

As a result, a dark field imaging system comprising an object receiving space, where such a phantom device is arranged will provide the respective advantage. The same holds for a method for acquiring an image, wherein the phantom device is scanned simultaneously or subsequently with the human subject, or in particular its region of interest.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

In the following, the phantom device 10 is exemplarily described as being used in the context of the dark field imaging system 12. But it should be noted, that the phantom device 10 may also be used for another dark field imaging system.

Figure 1:
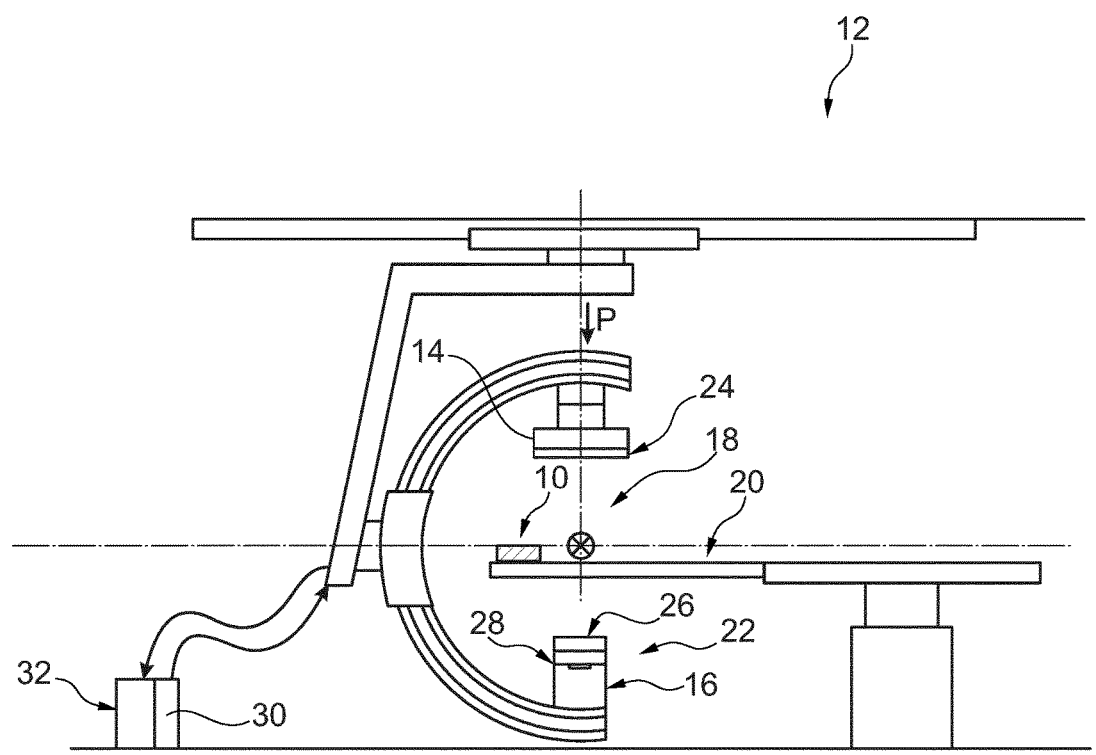
FIG. 1 schematically illustrates an example of an imaging system.

FIG. 1 schematically illustrates an embodiment of a dark field imaging system 12. The dark field imaging system 12 may also be referred to as an X-ray imaging system, a phase-contrast imaging system or a system. The dark field imaging system 12 comprises a source 14 for generating X-ray radiation. The source 14 may also refer to as an X-ray source. The dark field imaging system 12 further comprises a detector 16 for detecting X-ray radiation. The detector 16 may also be referred to as an X-ray detector. Further, the dark field imaging system 12 comprises a phantom device 10. Moreover, the dark field imaging system 12 comprises a receiving space 18. The receiving space 18 may also be referred to as an object receiving space. The receiving space 18 is arranged between the source 14 and the detector 16.

The dark field imaging system 12 further comprises a support device 20. The support device 20 is configured for supporting a human subject (not shown) and/or the phantom device 10. In an example, the human subject or a region of interest of the human subject may be arranged at the receiving space 18 without the support of the support device 20. In this case, just die phantom device may be supported by the support device 20. In a further example, both, the human subject (or at least a region of interest thereof) and the phantom device 10 may be supported by the support device 20.

Furthermore, the dark field imaging system 12 comprises an interferometer 22. The interferometer 22 may be configured as a Talbot grating interferometer. In an example, the interferometer 22 comprises a source grating 24, a phase grating 26 and an analyser grating 28. The interferometer 22 is configured for creating interference pattern. It is understood that, without repeating here all the explanations, examples, effects, features and/or advantages provided with reference to the interferometer explained in the introduction, the interferometer 22 of the dark field imaging system 12 of the invention may be configured in an analogous manner. Thus, all the explanations, examples, effects, features and/or advantages, although provided with reference to the interferometer described in the introduction, may be also to be intended as being provided at least in an analogous manner by the interferometer 22 of the dark field imaging system 12 of the present invention or the dark field imaging system 12 of the present invention as such.

The dark field imaging system 12 further comprises a control unit 30 for controlling the source 14 and the interferometer 22. The control unit 30 may comprise a control sub-unit for controlling the source 14 and a further control sub-unit for controlling the interferometer 22.

The dark field imaging system 12 further comprises a processing unit 32. The processing unit 32 is at least indirectly coupled to the detector 16 for receiving a detector signal from the detector 16 representing detected X-ray radiation. It should be noted that, even though the control unit 30 and the processing unit 32 are schematically shown in FIG. 1 as one integrated unit, this is not necessarily the case. Thus, the control unit 30 and the processing unit 32 may be integrated by one unit or may be formed by separated units, namely a control unit 30 being separated from the processing unit 32. Nevertheless, both units 30, 32 may be coupled via a communication connection for exchanging data and/or signals.

The supporting device 20 is configured to be arranged at least with a part thereof at the receiving space 18, such that X-ray radiation generated by the source 14 and transmitted through the human subject and the phantom device 10 is detectable by the detector 16. In an example, X-ray radiation generated by the source 14 may be transmitted simultaneously through the human subject and the phantom device. In another example, X-ray radiation generated by the source 14 may be subsequently transmitted through the human subject and the phantom device during a scan performed by the dark field imaging system 12.

The interferometer 22 is arranged between the source 14 and the detector 16. In this context, the source grating 24, the phase grating 26 and the analyser grating 28 may be arranged in a pathway of X-ray radiation provided by the source 14 towards the detector 16. Furthermore, the gratings 24, 26, 28 may be arranged, such that the object receiving space 18 is arranged between the source grating 24 and the phase grating 26. However, other configurations and/or arrangements of the gratings 24, 26, 28 may also be possible.

The control unit 30 is configured to cause a scan of a region of interest of the human subject and the phantom device. Thus, the region of interest of the human subject and the phantom device may be subject of the same scan caused by the control unit 30. The region of interest of the subject may be predefined. The control unit 30 may be configured to cause the scan, such that X-ray radiation generated by the source 14 is projected towards the region of interest of the human subject as well as towards the phantom device 10. It may be preferred, that X-ray radiation is simultaneously projected towards the region of interest of the human subject and the phantom device 10. But, it may also be preferred, that X-ray radiation provided by the source 14 may be subsequently projected towards the region of interest of the human subject and the phantom device 10.

The control unit 30 is configured to control the interferometer 22, and in particular the analyser grating 28 of the interferometer 22, such that the interferometer 22 influences X-ray radiation transmitted through the region of interest of the human subject and/or the phantom device 10. As a result, X-ray radiation impinging on the detector 16 comprises an interference pattern.

The processing unit 32 is configured to determine an image, in particular a dark field image, representing the region of interest of the human subject and the phantom device, based on a de-coherence component of the detector signal of the detector 16 caused by the scan.

The source grating 24 may be directly or indirectly connected to the source 24. Even though FIG. 1 schematically illustrates a direct contact of the source grating 24 and the source 14, this is not necessarily the case. Instead, the source grating 24 may be arranged at a predefined distance from the source 14. The source grating 24 may be configured to cause a spatial coherence of X-ray radiation emitted from the X-ray source 14. In an example, the source grating 24 may comprise a period to match said spatial coherence.

The phase grating 26 may also be referred to as an absorption grating. The phase grating 26 may comprise a period, which is preferably different from the period of the source grating 24. The phase grating may be arranged at a distance, in particular a predefined distance, from the source grating 24. Even though FIG. 1 schematically illustrates, that the phase grating 26 and the analyser grating 28 as well as the detector 16 are arranged one above the other, in practice, the phase grating 26 may be arranged at a predefined distance from the analyser grating 28. Further, the analyser grating 28 may be arranged at a predefined distance from the detector 16. However, in an example, the analyser grating 28 may be directly connected to the detector 16 or the detector 16 and the analyser grating 28 may be integrally formed.

Further, the phase grating 26 may be configured to cause interference pattern. Said interference pattern may be detected by the detector 16. Therefore, in an example, the interferometer 22 may just comprise the source grating 24 and the phase grating 26. However, a phase-shift of the interference pattern may not be directly spatially resolved by the detector 16. Therefore, in order to "sample" and/or detect the interference pattern, the analyser grating 28 may be arranged between the phase grating 26 and the detector 16. The actual extraction of the interference pattern may be achieved in a number of different ways. In an example, a relative motion between the detector 16 and at least one of the gratings 24, 26, 28 may be needed. This may be achieved by using an actuator, which is configured to laterally move one of the gratings, in particular the analyser grating 26. The lateral movement may be a movement in a direction perpendicular to the propagation direction P of X-ray radiation provided by the source 14 towards the detector 16. For instance, the analyser grating 28 may be subsequently moved to discrete grating positions and the detector 16 may be configured to measure the intensity of X-ray radiation at each grating position. The intensity of the X-ray radiation will then be found to oscillate in a sinusoidal fashion. This approach of "phase stepping" has been described by F. Pfeifer et al. in "A phase retrieval and differential phase-contrast imaging with low-brilliance X-ray sources" in Nature Phys. Lett. 2, 258-261 (2006). The oscillation intensity detected by the detector "encodes" a phase-shift of the intensity pattern along with the absorption caused by the human subject and/or the phantom device 10 and the de-coherence caused by the human subject and/or the phantom device 10. In this sense, at least one component of the detector signal provided by the detector 16 may represent an absorption component and another component of the detector signal may represent a de-coherence component.

In an example, the dark field imaging system 12 may be a rotational C-arm radiography system, as it is schematically shown in FIG. 1. However, the dark field imaging system 12 according to the present invention may also be another system, for example a CT imaging system.

Figure 7:
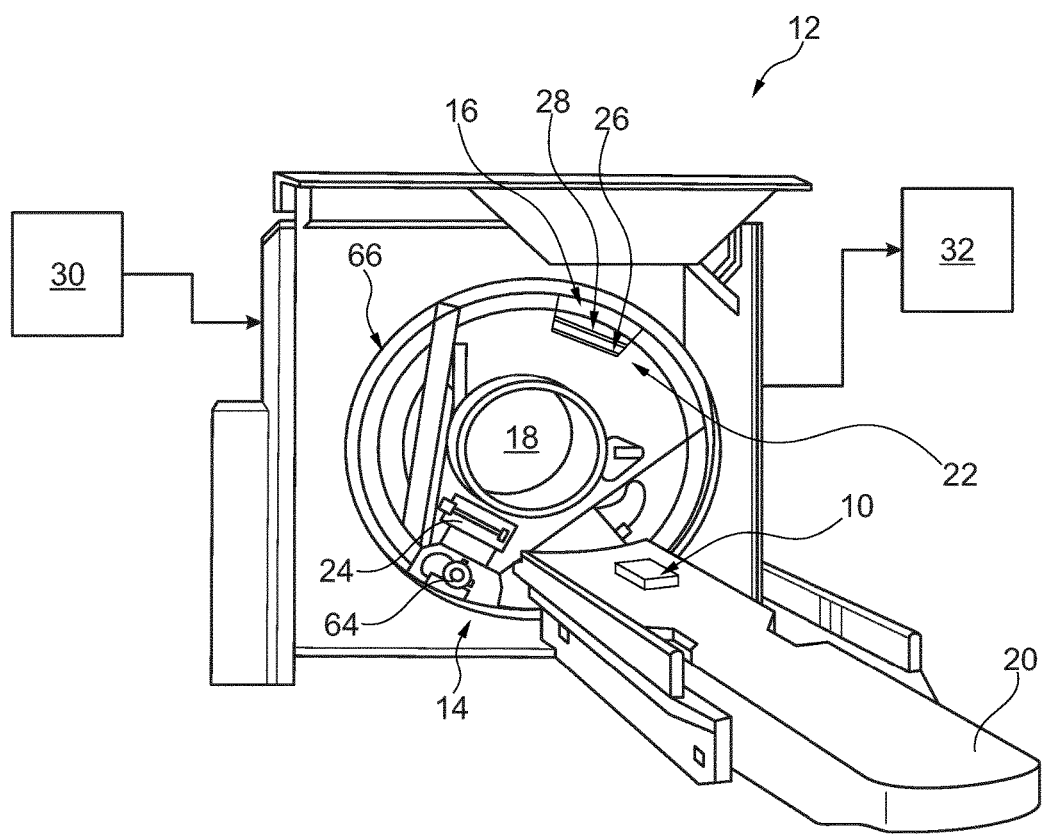
FIG. 7 schematically illustrates a further example of an imaging system.

FIG. 7 schematically illustrates a further embodiment of a dark field imaging system 12. In this case, the dark field imaging system 12 may be formed by a CT imaging system.

It is understood that, without repeating here all the explanations, examples, effects, features and/or advantages provided with reference to previously descripted embodiment of the dark field imaging system 12, the CT imaging system as a further embodiment of the dark field imaging system 12 is intended to be configured at least partly in an analogous manner. Thus, all the explanations, examples, effects, features and/or advantages, although provided with reference to previously descripted embodiment of the dark field imaging system 12, are also to be intended as being provided (where appropriated) by the CT imaging system as a further embodiment of the dark field imaging system 12. In the following, the CT imaging system as a further embodiment of the dark field imaging system 12 is exemplarily described in further detail.

The CT imaging system comprises a source 14 for generating X-ray radiation. The source 14 may comprise an X-ray tube 64. A source grating 24 is arranged at a predefined distance next to the X-ray tube 64.

Furthermore, the CT imaging system 12 comprises an interferometer 22. The interferometer 22 may be configured as a Talbot grating interferometer. In an example, the interferometer 22 comprises a source grating 24, a phase grating 26 and an analyser grating 28. Preferably, the source grating 24 is mounted to the source 14. The source 14 is preferably mounted to a gantry 66. The CT imaging system 12 further comprises a detector 16 for detecting X-ray radiation. The detector 16 is also preferably mounted to the gantry 66. The phase grating 26 and the analyser grating 28 are arranged on after the other to the detector or the gantry 66. It is to be noted in this context that the gratings 24, 26, 28 of the interferometer 22 are arranged in a pathway between the source 14 and the detector 16.

The source 14 and the detector 16 are arranged opposite to each other. A receiving space 18 is arranged between the source 14 and the detector 16. The receiving space 18 may also be referred to as an examination region. Furthermore, the phase grating 26 and/or the analyser grating 28 may be arranged between the receiving space 22 and the detector 16. The source grating 24 of the interferometer 22 is arranged between the source 14 and the receiving space 18. However, this is not necessarily the case. Other configurations of the gratings 24, 26, 28 are also possible.

The CT imaging system 12 further comprises a support device 20 for supporting a human subject and the phantom device 10. The support device 20 may be a table, a couch, a chair, or the like. The support device 20 is movable into and/or within the receiving space 18. The receiving space 18 is preferably defined by the gantry 66. Furthermore, the gantry 66 is preferably formed and/or adapted as a rotatable gantry 66. Thus, the gantry 66 may be rotatable around a predefined axis in order to rotate the source 14, the interferometer 22 and the detector 16 circumferentially about the receiving space 18.

The CT imaging system 12 further comprises the control unit 30 for controlling the source 14 and the interferometer 22. The control unit 30 may also be configured for controlling a rotation or a rotation position of the gantry 66. Furthermore, the control unit 30 may be configured for controlling a movement of the support device 20, in particular such that the support device 20 may be moved into the receiving space 18. For scanning purposes, the support device 20 is moved, in particular repeatedly stepped linearly, in order to perform a respective scan of the human subject and the phantom device 10.

The detector 16 is preferably configured to detect X-ray radiation during said scan. In particular, the detector 16 is configured to continuously detect X-ray radiation, while the support device 20 is moved towards and/or into the receiving space 18. Before describing the advantages, effects and/or preferred embodiments of the dark field imaging system 12 in further detail, an embodiment of the phantom device 10 should be described.

Figure 2:
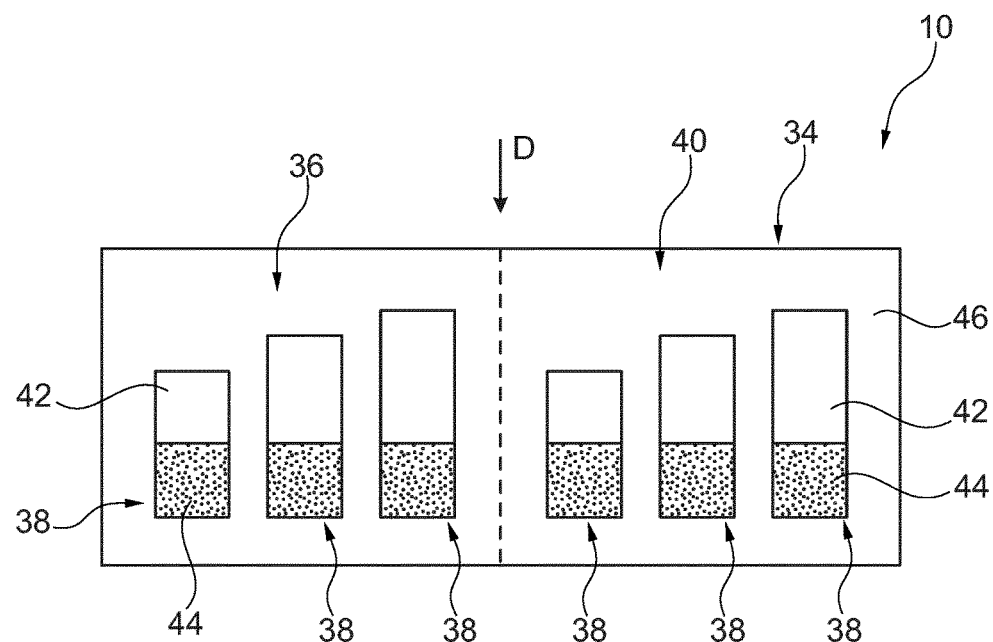
FIG. 2 schematically illustrates an example of a phantom device.

FIG. 2 schematically illustrates an embodiment of a phantom device 10 in a cross-sectional view. The phantom device 10 comprises a main body 34. The main body 34 comprises at least a first group 36 of at least two reference parts 38.

In the exemplarily shown embodiment in FIG. 2, the main body 34 comprises the first group 36 of three reference parts 38 and a second group 40 of three reference parts 38. Thus, the first group 36 may be formed of its three reference parts 38 and the second group 40 may be formed of its three reference parts. It should be noted that the reference parts 38 of the first group 36 are different between each other. Further, the reference parts 38 of the second group 40 are different between each other. Moreover, the reference parts 38 of the first group 36 are preferably different from the reference parts 38 of the second group 40. Furthermore, the reference parts 38 of the respective group 36, 40 may be formed as separated reference parts 38. Thus, the reference parts 38 of the respective group 36, 40 may be arranged with a gap between each other. Furthermore, the reference parts 38 of the respective group 36, 40 may be arranged in parallel. Moreover, the reference parts 38 of each group 36, 40 or of both groups 36, 40 may be aligned with respect to a predefined direction D of the main body 10.

Each reference part 38 is formed of a respective attenuation part 42 and a respective de-coherence part 44. The attenuation part 42 and the de-coherence part 44 of the same reference part 38 are stacked on top of each other. This holds for each of the reference parts 38 in an analogous manner. Thus, each reference part 38 is formed of the respective attenuation part 42 and the respective de-coherence part 44 being stacked on the respective attenuation part 42. Each reference part 38 is formed, such that the respective attenuation part 42 and the respective de-coherence part 44 are arranged consecutively along the predefined direction D of the main body 34.

As an effect, if the phantom device 10 is arranged in the object receiving space 18 of the dark field imaging system 12, X-ray radiation provided by the source 14 may be projected along the predefined direction D, if the propagation direction P of said X-ray radiation coincides with the predefined direction D of the main body 34. For this purpose, the phantom device 10 may be arranged on and/or releasably connected with the support device 20, such that the propagation direction P and the predefined direction D coincide at least for one time instance or period with each other. In particular, the propagation direction P and the predefined direction D may coincide for a time period of the scan with each other, when the phantom device 10 is to be scanned. As a result, X-ray radiation may pass an attenuation part 42 and a de-coherence part 44 of the same reference part 38 one after the other. In particular, the phantom device 10 may be arranged on the support device 20, such that X-ray radiation passes initially the attenuation part 42 of a reference part 38 and thereafter the respective de-coherence part 44, or vice versa. This may hold in an analogous manner for each of the reference parts 38.

Each attenuation part 42 is configured to cause attenuation disturbance to an X-ray beam, if said X-ray beam passes the respective attenuation part 42 along the predefined direction D. Further, each de-coherence part 44 is configured to cause de-coherence disturbance to an X-ray beam, if said X-ray beam passes the respective de-coherence part along the predefined direction D.

Furthermore, each of the de-coherence parts 44 of the first group 36 are configured to cause the same first degree of de-coherence disturbance. The attenuation parts 44 of the first group 36 are configured to cause mutually different degrees of attenuation disturbance.

It is further preferred, that each of the de-coherence parts 44 of the second group 40 are configured to cause the same second degree of de-coherence disturbance, wherein the attenuation parts 42 of the second group 40 are configured to cause mutually different degrees of attenuation disturbance.

As it is schematically shown in FIG. 2, the first group 36 and the second group 40 are separately arranged, which is indicated by the dashed line in the middle of the main body 34. However, the dashed line is shown rather for illustrating purposes. According to a preferred embodiment, the reference parts 38 are integrated into and surrounded by a casting component 46 of the main body 34. The casting component may be a casting compound and/or a cured resin, in particular a cured epoxy resin.

If X-ray radiation is imposed on the main body 34 in the predefined direction D, the X-ray radiation transmits initially through the attenuation parts 42 of the reference parts 38. Thereafter, the respectively transmitted X-ray radiation is transmitted through the respective de-coherence part 44. Due to the mutually different degrees of attenuation disturbance of the attenuation parts 42 of each group 36, 40, the X-ray radiation passing out of each attenuation part 42 may have a different spectrum as the X-ray radiation with respect to X-ray radiation initially imposed on the main body 34 of the phantom device 10.

As a result, each of the de-coherence parts 44 of each group 36 and 40 are imposed with X-ray radiation having mutually different X-ray wavelength spectra. Thus, even though the de-coherence parts 44 of the same group 36, 40 may be configured to cause the same degree of de-coherence disturbance, the X-ray radiation passing out each de-coherence part 44 of the same group 36 may be subject of a different impact of the respective de-coherence disturbance. In other words, even though the de-coherence disturbance caused by each de-coherence part 44 of the same group 36, 40 may be similar, the impact of said de-coherence disturbance may depend on the spectrum of the X-ray radiation, by which the respective de-coherence part is imposed by.

As an effect, the phantom device 10 allows to show different disturbance effects with respect to X-ray radiation provided by the source 14, which may occur in a similar manner with respect to different portions of a region of interest of the human subject. In particular, each of said portions of the human subject may provide mutually different degrees of attenuation disturbance, wherein the portions may comprise parts which cause at least basically the same degree of de-coherence disturbance. For example, this may occur, if a lung region of a human subject is to be imaged during a scan.

As an effect, the phantom device 10 may be used to quantify and/or classify the disturbances and therefore provides the possibility, to better assess an image part of an image acquired via a dark field imaging system representing a dark field image part of the human subject. This part of the dark field image may be assessed in view of and/or relatively with regard to the image part which represents the phantom device 10.

As a further effect, the same region of interest of the human subject may be scanned at different times with the same phantom device 10, in particular even with different dark field imaging systems 12 or with the same dark field imaging system 12, wherein different settings for the dark field imaging system 12 may be used or not.

Figure 4:
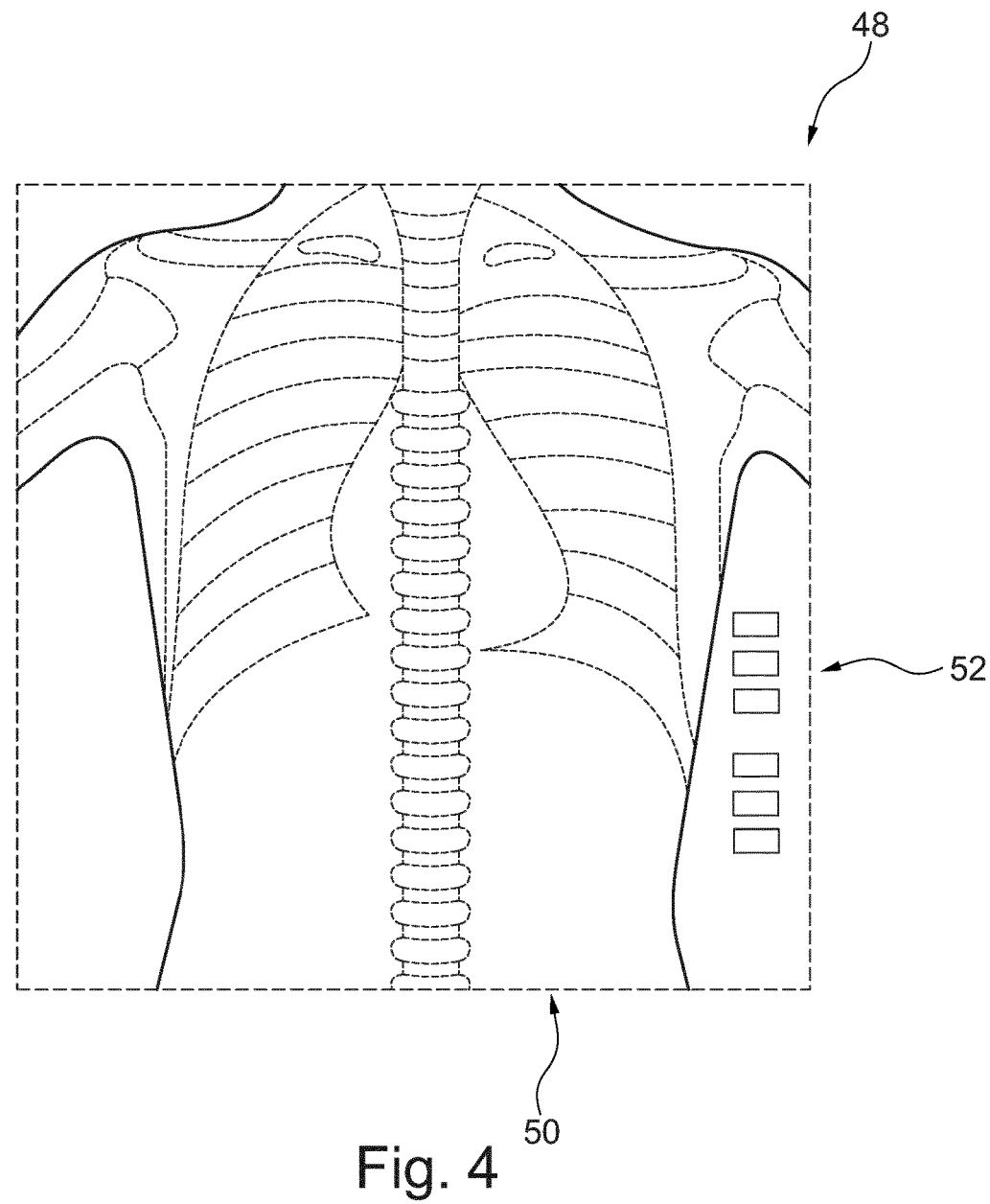
FIG. 4 schematically illustrates a dark field image.

FIG. 4 schematically shows a dark field image 48 of a region of interest of a human subject and a phantom device 10 acquired by a scan with the dark field imaging system 12. As a result, the dark field image 48 illustrates in a first image part 50 the region of the human subject and in a further image part 52 the phantom device 10.

Independent of the conditions or the choice of the dark field imaging system 12, the resulting images 48 may be reliably compared and/or assessed, since each of said images 48 may show at least a part indicating and/or representing the phantom device 10. Thus, the respective part 52 of the image 48 representing the phantom device 10 may function as a reference for qualitatively and/or quantitatively assessing the respective image part 50 and therefore allow a respective and reliable assessment, in particular in comparison to each other.

Figure 3:
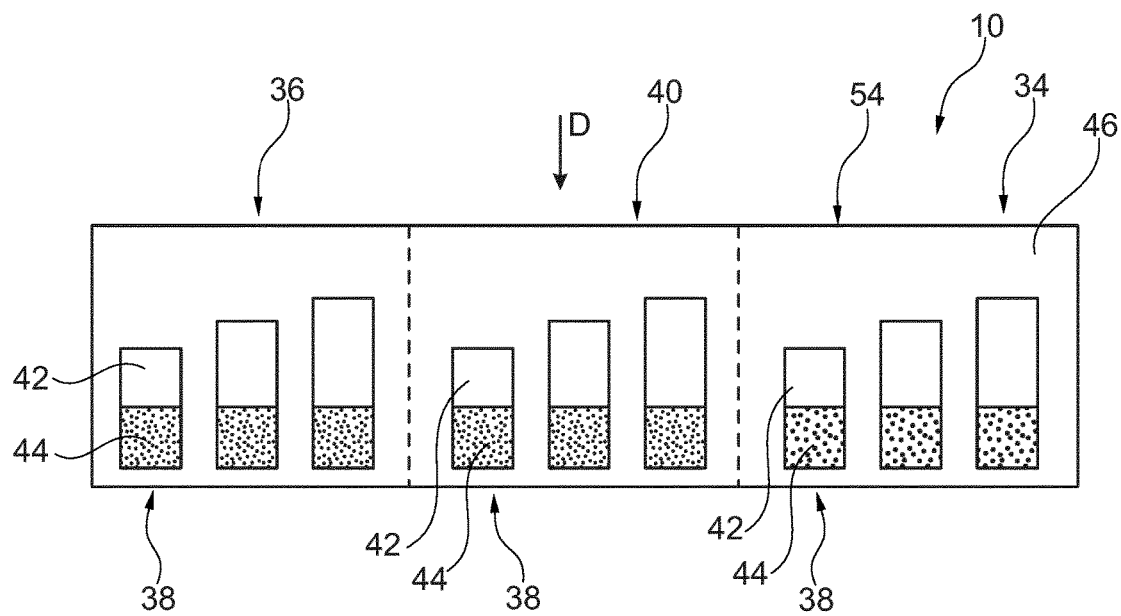
FIG. 3 schematically illustrates a further example of a phantom device.

FIG. 3 schematically illustrates a further embodiment of the phantom device 10 in a cross-sectional view. The phantom device 10 basically corresponds to the phantom device 10, as it is shown and correspondingly described with respect to FIG. 2. Therefore, reference is made in an analogous manner with respect to the previously provided explanations, examples, preferred features and/or effects, which have been described for the phantom device 10 in view of FIG. 2. The phantom device 10 shown in FIG. 3 comprises a further group 54, which is also referred to as the third group 34. Thus, the main body 34 may also comprise the third group 54 of at least two reference parts 38, and in particular of three reference parts 38. The third group 54 is preferably formed by said three reference parts 38. The following explanations regarding the groups 36, 40, 54 may also apply for the phantom device 10 as exemplarily shown in FIG. 3 and/or at least in an analogous manner for a phantom device 10 as it is exemplarily shown in FIG. 2.

According to a preferred example of the phantom device 10, the main body 34 comprises the second group of at least two reference parts 38, wherein each of the de-coherence parts 44 of the second group 40 is configured to cause the same second degree of de-coherence disturbance, wherein the attenuation parts 42 of the second group 40 are configured to cause mutually different degrees of attenuation disturbance, and wherein the de-coherence parts 44 of the first and second group 36, 40 are configured, such that the first degree of de-coherence disturbance is different from the second degree of de-coherence disturbance. In an example, the main body 34 comprises the third group 54 of the at least two reference parts 38, wherein each of the de-coherence parts 44 of the third group 54 are configured to cause the same third degree of de-coherence disturbance, wherein the attenuation parts 42 of the third group 54 are configured to cause mutually different degrees of attenuation disturbance, and wherein the de-coherence parts 44 of the first, second and third group 36, 40, 54 are configured, such that the first degree of de-coherence disturbance, the second degree of de-coherence disturbance and the third degree of de-coherence disturbance are mutually different.

As a result of the different degrees of de-coherence disturbance with respect to the de-coherence parts 44 of the first group 36 and the second group 40 and/or with respect to the de-coherence parts 44 of the first, second and third group 36, 40 and 54, the disturbances provided by the respective phantom device 10 may be used to imitate disturbances caused by different portions of a human subject. As an effect, a clinician using such a phantom device 10 during a scan with the dark field imaging system 12 may be in the position to reliably assess, classify and/or compare images of the human subject, for instance acquired at different time instances and/or with settings for the dark field imaging system 12 or even with the use of different dark field imaging systems 12.

Figure 5:
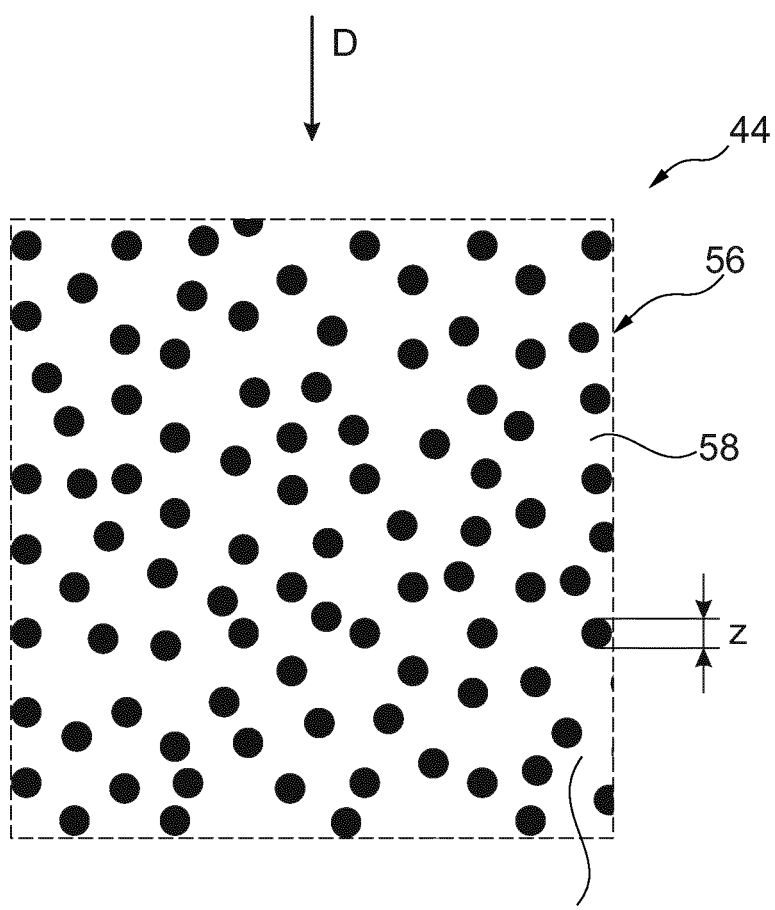
FIG. 5 schematically illustrates an example of a de-coherence part.

FIG. 5 schematically illustrates a de-coherence part 44 in an enlarged view. In an example, each de-coherence part 44 comprises a micro-structure 56 configured to cause X-ray scattering, in particular small angle X-ray scattering, to an X-ray beam, if said X-ray beam passes the respective de-coherence part 44 in the predefined direction D. It should be noted, that the micro-structure 56 is shown in FIG. 5 just in an illustrating manner. In particular, the scattering angle caused by the micro-structure may be smaller than 0.1 mrad or smaller than 1.5 mrad. The micro-structure 56 of each de-coherence part 44 may be formed by a plurality of micro-spheres 58. The micro-spheres 58 of each respective de-coherence part 44 may be integrated in a resin 60 of the respective de-coherence part 44. The resin 60 may be a cured resin, in particular a cured epoxy resin. Each micro-sphere 58 may refer to a spherical particle or to a globular particle. Each of the micro-spheres 58 may be formed by a solid material or may be filled with a gas.

The micro-spheres 58 of the respective de-coherence part 44 may be randomly distributed within the resin 60 of the respective de-coherence part 44.

Furthermore, the micro-spheres 58 of the first group 36 may be formed by and/or filled with a first material. The micro-spheres 58 of the second group may be formed by and/or filled with a second material. The micro-spheres 58 of the third group 54 may be formed by and/or filled with a third material. Furthermore, it is preferred that the first material is different from the second material. Moreover, it may be preferred, that the first, second and third material may be mutually different material.

As a result, the first degree of de-coherence disturbance may be different from the second degree of de-coherence disturbance. Moreover, the first, second and third degree of de-coherence disturbance may be mutually different.

In particular, if the phantom device 10 is used with respect to the scanning of a human subject, it has been shown of advantage, if a size z of each of the micro-spheres 58 is between 10 μm and 300 μm. Preferably, a size z of a micro-sphere 58 may refer to a structure size of the respective micro-sphere 58, in particular to its average outer diameter.

In an example, a size z of each of the micro-spheres 58 of the de-coherence parts 44 of the first group is between 170 μm and 190 μm. In an example, a size z of each of the micro-spheres 58 of the de-coherence parts 44 of the second group 40 is between 210 μm and 230 μm. In a further example, a size z of each of the micro-spheres 58 of the de-coherence parts 44 of the third group 54 is between 190 μm and 210 μm.

As a result, in particular resulting from different sizes z of the micro-spheres 58 of the respective de-coherence parts 44, a phantom device 10 being scanned together with a region of interest of a human subject may provide the ability, to quantitatively and/or qualitatively assess and/or classify image values of the image 48, which relate to the part 50 of said image 48, which represents the human subject, or in particular a region thereof.

According to a further example, the micro-spheres 58 of the same group 36, 40, 54 (respectively) are each of the same size z. As a result, the de-coherence parts 44 of the same group 36, 40, 54 (respectively) may cause the same degree of de-coherence disturbance.

As a further effect, the de-coherence parts 42 of the same group 36, 40, 54 (respectively) result in mutually different degrees of attenuation disturbance, which may result in different wavelength spectra of the X-ray radiation, which passes out of the respective attenuation part 42 and thereafter passes into the corresponding de-coherence part 44.

As a further effect, the de-coherence parts 44 of the same group 36, 40, 54 (respectively) may be imposed by X-ray radiation, wherein the respective X-ray radiation for the de-coherence part 44 may differ in their wavelength spectra. As a consequence, X-ray radiation passing out of the respective de-coherence parts 44 may also be different with respect to their wavelength spectra, wherein the spectra may be mutually different affected by the de-coherence parts 44. Since similar effects may occur for different portions of the human subject, the phantom device 10 may be used to reliably and easily assess and/or classify image values of the image 48, which represent the respective part of the human subject.

In an even further example, the micro-spheres 58 of the first group 36 may be of a different size z than the micro-spheres 58 of the second group 40. In particular, the micro-spheres of the first, second and third group may be groupwise of mutually different sizes z. As a result, the micro-spheres 58 of each respective group 36, 40, 54 may imitate a respective structure of a human subject, in particular of different portions of the human subject.

Figure 6:
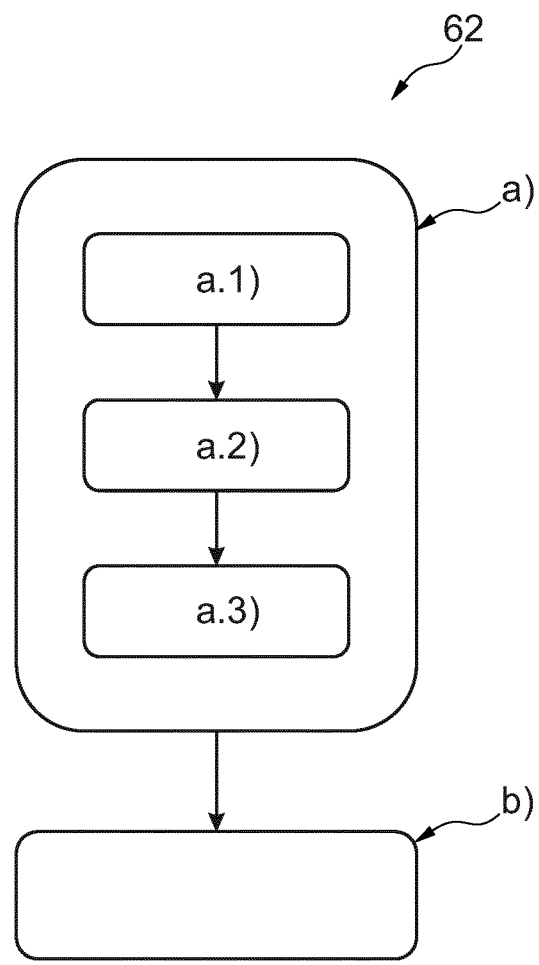
FIG. 6 schematically illustrates a method.

FIG. 6 schematically illustrates an example of the method 62 for acquiring an image 48. The method 62 may comprise the steps a) and b).

In the first step a), a scan of a region of interest of the human subject and a phantom device 10 is performed. With respect to the phantom device 10, reference is made to the previously provided explanations, preferred features, effects and/or advantages. Step a) comprises the following sub-steps a.1), a.2) and a.3): In step a.1), X-ray radiation is generated by source 14, such that X-ray radiation is transmitted or emitted towards the region of interest of the human subject and the phantom device resulting in transmitted X-ray radiation.

In the step a.2), the transmitted X-ray radiation is influenced by an interferometer 22 resulting in influenced X-ray radiation.

In step a.3), the influenced X-ray radiation is detected by a detector 16 resulting in a detector signal.

In step b), an image 48, representing the region of interest of the human subject and the phantom device 10, is determined based on a de-coherence component of the detector signal.

It is understood that, without repeating here all the explanations, examples, effects, features and/or advantages provided with reference to the phantom device 10 and/or the dark field imaging system 12, the method 62 of the invention is intended to be configured to carry out the method steps for which the dark field imaging system 12 is configured to. Thus, all the above provided examples, explanations, effects, features and/or advantages, although provided previously with reference to the phantom device 10 and/or the dark field imaging system 12, are also to be intended as being provided in an analogous manner for the method 62.

According to a further example of the present invention, a computer program element is provided, which, when being executed by a processing unit is adapted to carry out the method described above.

According to further example of the present invention, a computer readable medium having stored thereon a program element is provided, which, when being executed by a processing unit is adapted to carry out the method described above.

The computer program element might be stored on a computer unit, which might also be part of an embodiment of the present invention. This computing unit may be adapted to perform or induce a performing of the steps of the method described above. Moreover, it may be adapted to operate the components of the above described apparatus. The computing unit may be adapted to operate automatically and/or to execute the orders of a user. A computer program may be loaded into a working memory of a data processor. The data processor may thus be equipped to carry out the method of the invention.

It has to be noted that embodiments of the invention are described with reference to different subject matters. In particular, some embodiments are described with reference to a phantom device 10 whereas other embodiments are described with reference to the dark field imaging system 12. However, a person skilled in the art will gather from the above that, unless otherwise notified, in addition to any combination of features belonging to one subject matter also any combination between features relating to different subject matters is considered to be disclosed with this application. However, all features may be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments may be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. An element or unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A phantom device for a dark field imaging system, the phantom device comprising:
    a main body,
    reference parts formed of an attenuation part and a de-coherence part being stacked on the attenuation part, such that the attenuation part and the de-coherence part of the respective reference part are arranged consecutively along a predefined direction of the main body;
    wherein each de-coherence part is configured to cause de-coherence disturbance to an X-ray beam, if said X-ray beam passes the respective de-coherence part along the predefined direction;
    wherein each attenuation part is configured to cause attenuation disturbance to an X-ray beam, if said X-ray beam passes the respective attenuation part along the predefined direction;
    wherein the main body comprises a first group of at least two reference parts;
    wherein each of the de-coherence parts of the first group are configured to cause the same first degree of de-coherence disturbance; and
    wherein the attenuation parts of the first group are configured to cause mutually different degrees of attenuation disturbance.

2. Phantom device according to claim 1,
    wherein the main body comprises a second group of at least two reference parts;
    wherein each of the de-coherence parts of the second group are configured to cause the same second degree of de-coherence disturbance;
    wherein the attenuation parts of the second group are configured to cause mutually different degrees of attenuation disturbance; and
    wherein the de-coherence parts of the first and second group are configured, such that the first degree of de-coherence disturbance is different from the second degree of de-coherence disturbance.

3. Phantom device according to claim 1, wherein each group comprises at least three reference parts.

4. Phantom device according to claim 1, wherein each reference part comprises a constant cross-section in a plane perpendicular to the predefined direction.

5. Phantom device according to claim 1, wherein each de-coherence part comprises a micro-structure configured to cause small-angle X-ray scattering to an X-ray beam, if it passes the respective de-coherence part in the predefined direction.

6. Phantom device according to claim 1, wherein the micro-structure of each de-coherence part is formed by a plurality of micro-spheres integrated in a resin of the respective de-coherence part.

7. Phantom device according to claim 1, wherein the micro-spheres of the first group are each formed by and/or filled with a first material, wherein the micro-spheres of the second group are each formed by and/or filled with a second material, and wherein the first material is different from the second material.

8. Phantom device according to claim 6, wherein a size of each of the micro-spheres is between 10 µm and 300 µm.

9. Phantom device according to claim 6, wherein the micro-spheres of the same group are each of the same size.

10. Phantom device according to claim 6, wherein the micro-spheres of the first group and the micro-spheres of the second group are of a different size.

11. Phantom device according to claim 1, wherein the reference parts are integrated into and surrounded by a casting compound of the main body.

12. A dark field imaging system, comprising:
    a source for generating X-ray radiation;
    a detector for detecting X-ray radiation;
    a phantom device according to claim 1;
    a receiving space arranged between the source and the detector;
    a support device for supporting a human subject and/or the phantom device;
    an interferometer for creating interference pattern;
    a control unit for controlling the source and the interferometer; and
    a processing unit coupled to the detector for receiving a detector signal from the detector representing detected X-ray radiation;
    wherein the support device is arrangeable at the receiving space, such that X-ray radiation generated by the source and transmitted through the human subject and the phantom device is detectable by the detector;
    wherein the interferometer is arranged between the source and the detector;
    wherein the control unit is configured to cause a scan of a region of interest of the human subject and the phantom device, such that X-ray radiation generated by the source is projected towards the region of interest of the human subject and the phantom device;
    wherein the control unit is configured to control the interferometer, such that the interferometer influences X-ray radiation transmitted through the region of interest of the human subject and/or the phantom device; and
    wherein the processing unit is configured to determine an image, representing the region of interest of the human subject and the phantom, based on a de-coherence component of the detector signal of the detector caused by the scan.

13. A method for acquiring an image, comprising:
performing a scan of a region of interest of a human subject and a phantom device according to claim 1, wherein the performing comprises:
- generating X-ray radiation by a source, such that the X-ray radiation is transmitted towards the region of interest of a human subject and the phantom device resulting in transmitted X-ray radiation,
- influencing the transmitted X-ray radiation by an interferometer resulting in influenced X-ray radiation, and
- detecting the influenced X-ray radiation by a detector resulting in a detector signal; and determining an image, representing the region of interest of the human subject and the phantom device, based on a de-coherence component of the detector signal.

14. A non-transitory computer readable medium having stored one or more executable instructions, which when executed by a processor, cause the processor to perform a method claim 13.

\* \* \* \* \*